(12) United States Patent
Wang (10) Patent No.: US 7,908,679 B2
(45) Date of Patent: Mar. 22, 2011

(54) SAFETY GOGGLES STRUCTURE

(75) Inventor: Ming-Chun Wang, Taipei (TW)

(73) Assignee: T-Link PPE Ltd., Taipei (TW)

( * ) Notice: Subject to any disclaimer, the term of this patent is extended or adjusted under 35 U.S.C. 154(b) by 532 days.

(21) Appl. No.: 12/143,236

(22) Filed: Jun. 20, 2008

(65) Prior Publication Data
US 2009/0313746 A1 Dec. 24, 2009

(51) Int. Cl.
*A61F 9/02* (2006.01)
(52) U.S. Cl. .......................................................... 2/431
(58) Field of Classification Search ............. 2/426–429, 2/431, 447, 448; 351/43
See application file for complete search history.

(56) References Cited

U.S. PATENT DOCUMENTS

| 5,617,588 | A * | 4/1997 | Canavan et al. | 2/428 |
| 2008/0301857 | A1* | 12/2008 | Wang-Lee | 2/431 |
| 2009/0222979 | A1* | 9/2009 | Wang | 2/431 |
| 2010/0064421 | A1* | 3/2010 | Wang-Lee | 2/428 |

* cited by examiner

*Primary Examiner* — Katherine Moran
(74) *Attorney, Agent, or Firm* — WPAT, P.C.; Anthony King (57) ABSTRACT

The present invention discloses a safety goggles structure having a frame connecting portion, a frame latch portion, two frame snap-in portions, a lens connecting portion, a lens latch portion, two lens snap-in portions and two elastic buckles to mount a lens onto a frame for achieving the effect of securely connecting the frame and the lens or improving their connecting stability. With an upper guide channel slantingly and concavely disposed on the frame and a lower guide channel vertically up-and-down and concavely disposed on the frame, gases and liquids can pass through without producing fogs and accumulating liquid on the lens, and foreign substances cannot enter into the safety goggles easily to cause any safety issue. With the design of an upper gutter on the frame, liquid splashed onto the safety goggles can flow along either side of the upper gutter to prevent liquid accumulation or leaking.

11 Claims, 11 Drawing Sheets

SAFETY GOGGLES STRUCTURE

FIELD OF THE INVENTION

The present invention relates to a safety goggles structure, and more particularly to a safety goggles structure capable of improving the connecting stability and preventing fogs and liquid accumulations or leaks.

BACKGROUND OF THE INVENTION

At a general construction site, workers usually wear a pair of goggles to protect their eyes from foreign matters such as dusts, pebbles and liquid splashes produced during constructions.

Traditional goggles are nothing more than a structure composed of a frame and lenses latched and connected with each other, but the design of the latch and connected structure is very simple, and thus the frame and the lenses may be easily separated from each other when the goggles are worn or removed.

In addition, fogs are easily produced on the lenses of the goggles in the situation when the temperature changes or when the workers inhale and exhale, and thus causing a safety issue during construction. To overcome the issue of having fogs on the lenses, the present safety goggles come with the design of air holes, but the air holes constitute a leak of the safety goggles, and the foreign matters such as dusts, pebbles, and liquid splashes still have chances to enter into the safety goggles or damage the eyes of construction workers.

Figure 4:
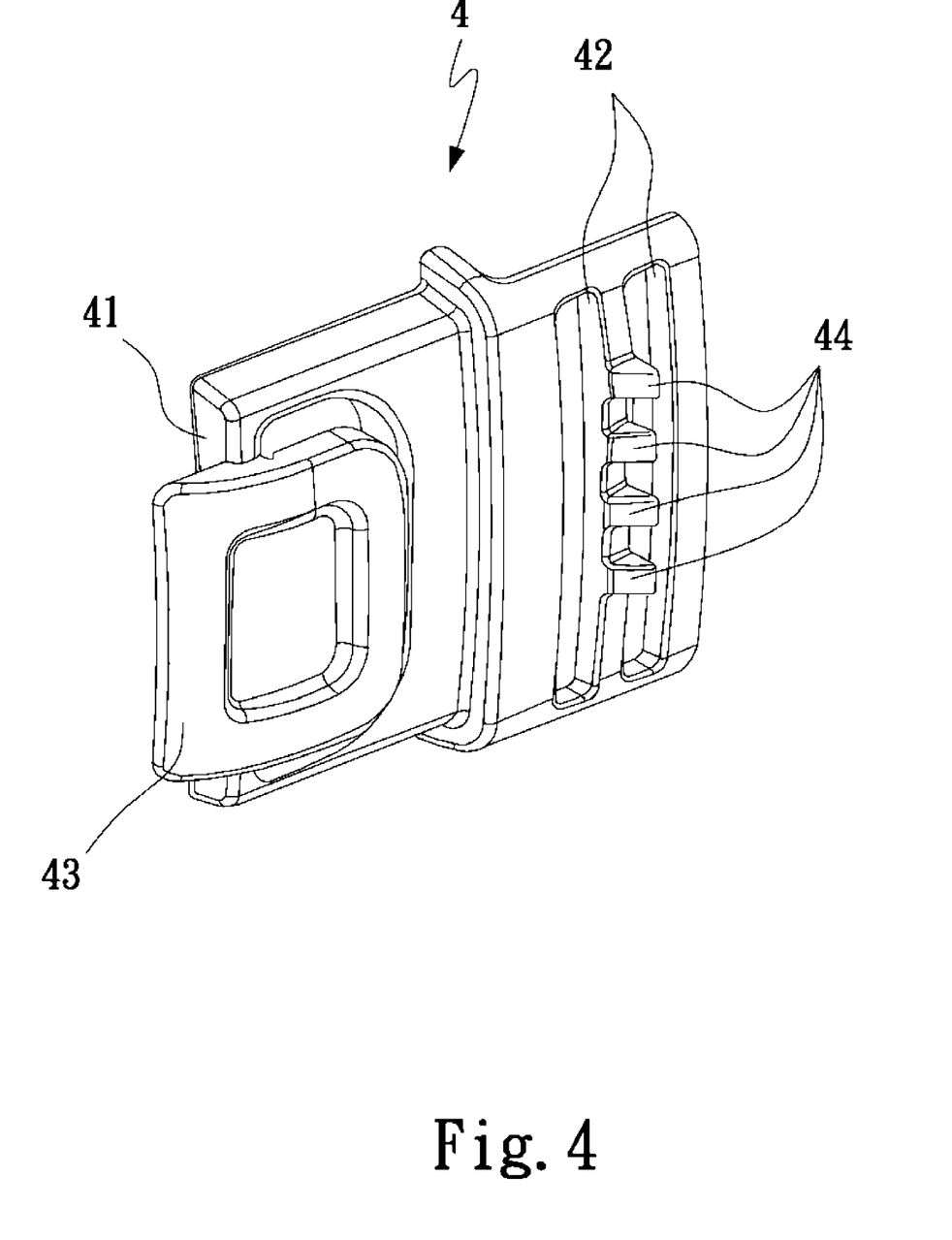
FIG. 4 is a perspective view of an elastic buckle in accordance with a preferred embodiment of the present invention.

Referring to FIG. 4 for U.S. Pat. Application No. 2004/0117898, a design of safety goggles for providing an anti-fog effect and protecting eyes is disclosed. However, if liquid splashes (such as rain water) enter into the safety goggles, liquid splashes are accumulated in the air holes to clog the air holes and disables the function of the air holes. After the liquid is accumulated constantly, the issues of overflows and leaks arise.

Therefore, it is a subject of the present invention to develop a safety goggles structure capable of improving the connecting stability of the safety goggles structure and preventing fogs, liquid accumulations and leaks.

SUMMARY OF THE INVENTION

In view of the foregoing shortcomings of the prior art, the inventor of the present invention has conducted extensive researches and experiments based on years of experience in the related field and finally invented a safety goggles structure to achieve the effect of improving the connecting stability of the safety goggles structure and preventing fogs, liquid accumulations and leaks.

The primary objective of the present invention is to provide a safety goggles structure for improving the connecting stability of the safety goggles structure and preventing fogs, liquid accumulations and leaks.

To achieve the foregoing objective, the safety goggles structure of the invention comprises:

a frame substantially in a ring-shape and having an opening around the frame, and the frame includes a frame connecting portion, a frame latch portion, two frame snap-in portions, at least one upper guide channel, at least one lower guide channel and an upper gutter, wherein the frame connecting portion is disposed at the top of the frame, and the frame latch portion is disposed at the bottom of the frame, and the two frame snap-in portions are disposed respectively on both lateral sides of the frame, and the upper guide channel is slantingly and concavely disposed at the front side of the top of the frame and interconnected to the opening and the exterior of the frame, and the lower guide channel is vertically up-and-down and concavely disposed at the bottom of the front side of the frame and interconnected to the opening and the exterior of the frame, and the upper gutter is concavely disposed at an upper side of the frame, and each of the two frame snap-in portions has a stop portion separately;

a lens, covered onto the opening, and having a periphery covered onto the upper guide channel and the lower guide channel, and the lens having a lens connecting portion, a lens latch portion and two lens snap-in portions, wherein the lens connecting portion is disposed at the top of the lens and latched to the frame connecting portion, and the lens latch portion is disposed at the bottom of the lens and latched to the frame latch portion, and the two lens snap-in portions are disposed on both lateral sides of the lens and latched to the two frame snap-in portions respectively, and each of the two lens snap-in portions includes a snap-in hole separately;

and two elastic buckles, having a top pressing edge separately, and inserted and latched into the two snap-in holes respectively, wherein the two top pressing edges abut the two stop portions respectively.

With the aforementioned design of various latch structures, the present invention achieves the effect of securely connecting the frame and the lens when the goggles structure is in use, so as to improve the connecting stability.

With the upper guide channel slantingly and concavely disposed at the top of the front side of the frame and upwardly tapered and the lower guide channel disposed at the bottom of the front side of the frame and upwardly tapered, air enters from the bottom and discharges from the top when the safety goggles structure of the invention is in use, so as to achieve the effect of distributing gases. In other words, the lens will not produce fogs. With the slanting design, foreign substances such as dusts, pebbles and liquid splashes will not enter into the safety goggles easily or damage the eyes of workers. The upper guide channel and the lower guide channel come with an upwardly tapered design. From conservation of mass, if air flows from a large cross-sectional area to a small cross-sectional area, the speed of the air flow will become larger, such that a jet flow is formed when the air enters into the lens and then discharges from the lens. In addition to the improvement of the anti-fog effect in the lens, the present invention can also enhance the heat dissipating effect.

With the upwardly tapered design of the upper guide channel and the upper gutter, liquid splashed onto the safety goggles will not enter into the safety goggles easily, since the upwardly tapered upper guide channel provides a small outlet for discharging the airflow. The liquid splashes will flow down along both lateral sides of the upper gutter without causing the issue of accumulating liquid. If liquid overflows from the upper guide channel into the safety goggles, the liquid will flow down along the slanting and concaved upper guide channel and the internal surface of the lens to the lower guide channel vertically up-and-down and concavely disposed at the bottom so as to effectively avoid liquid from contacting a wearer's eyes.

DESCRIPTION OF THE PREFERRED EMBODIMENT

The above and other objects, features and advantages of the present invention will become apparent from the following detailed description taken with the accompanying drawings.

Figure 1:
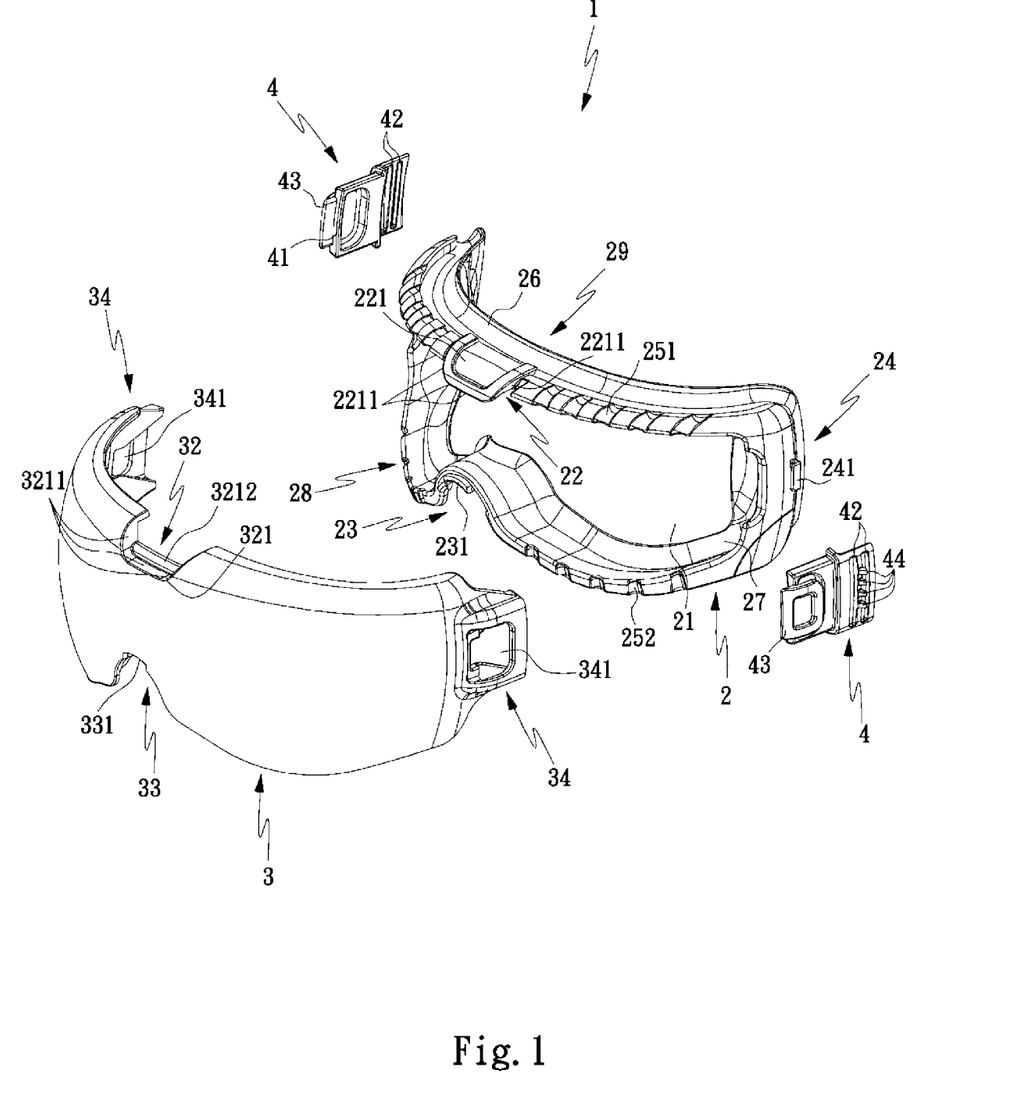
FIG. 1 is an exploded view of a preferred embodiment of the invention.

Referring to FIG. 1 for an exploded view of a preferred embodiment of the present invention, a safety goggles structure 1 of the invention comprises a frame 2, a lens 3 and two elastic buckles 4.

Figure 2:
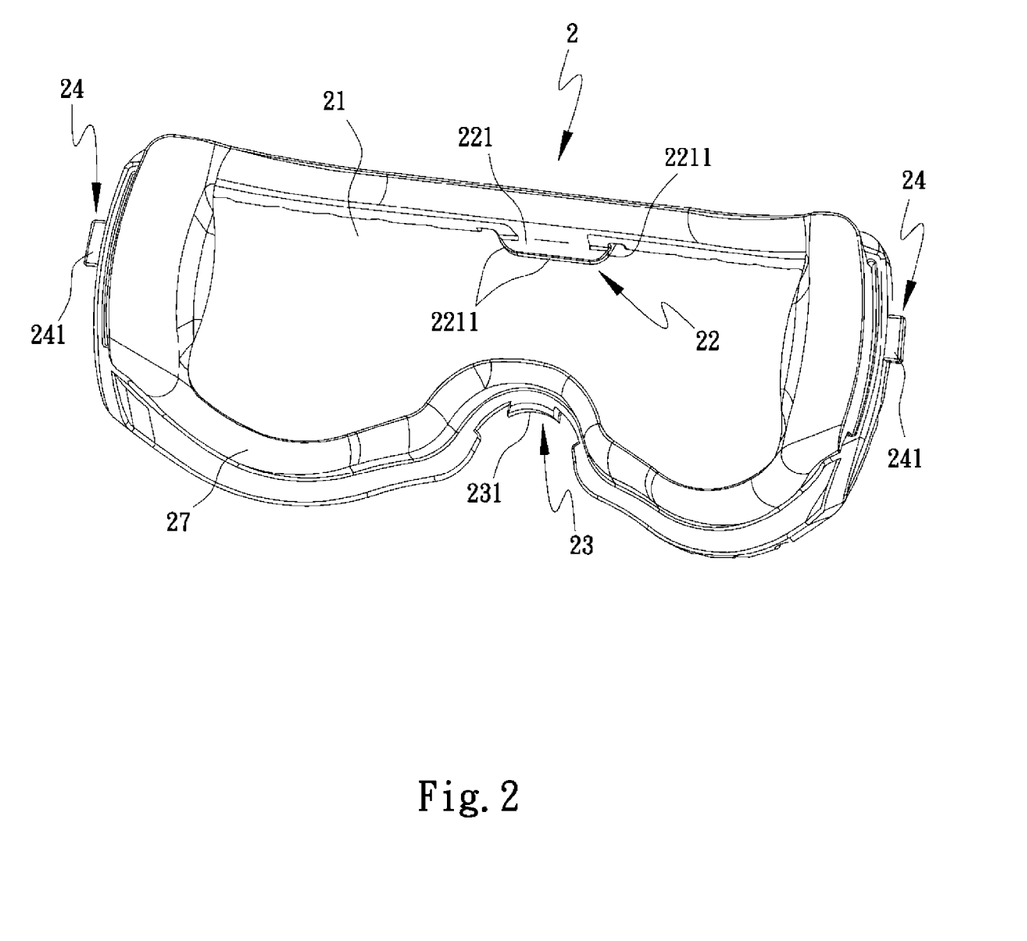
FIG. 2 is a perspective view of a frame in accordance with a preferred embodiment of the invention from another viewing angle.

With reference to FIGS. 1 and 2, FIG. 2 shows a perspective view of a frame in accordance with a preferred embodiment of the invention from another viewpoint, the frame 2 is substantially in a ring-shape and has an opening 21 around the frame 2, and the frame 2 includes a frame connecting portion 22, a frame latch portion 23, two frame snap-in portions 24, at least one upper guide channel 251, at least one lower guide channel 252 and an upper gutter 26. The frame connecting portion 22 is disposed at the top of the frame 2, and the frame latch portion 23 is disposed at the bottom of the frame 2, and two frame snap-in portions 24 are disposed on both lateral sides of the frame 2 respectively, and the upper guide channel 251 is upwardly tapered and slantingly and concavely disposed at the top of the front side of the frame 2 and interconnected with the opening 21 and the exterior of the frame 2, and the lower guide channel 252 is upwardly tapered and concavely disposed at the bottom of the front side of the frame 2 and interconnected to the opening 21 and the exterior of the frame 2, and the upper gutter 26 is disposed at the upper side of the frame 2, and each frame snap-in portion 24 includes a stop portion 241.

In this embodiment, the frame connecting portion 22 is a baffle 221, and the baffle 221 has an external baffle periphery 2211, and the frame latch portion 23 has a latch protrusion 231, and two stop portions 241 are L-shaped embedding hooks disposed on both lateral sides of the frame 2 respectively, and the frame 2 is divided into a front portion 28 and a rear portion 29, and the front portion 28 of the frame 2 is made of a hard material, and the rear portion 29 of the frame 2 is made of a soft material, and the rear portion 29 of the frame 2 is attached to the front portion 28 of the frame 2 after a secondary processing, and the soft material made rear portion 29 of the frame 2 provides a comfortable wearing of the safety goggles structure 1.

Figure 3:
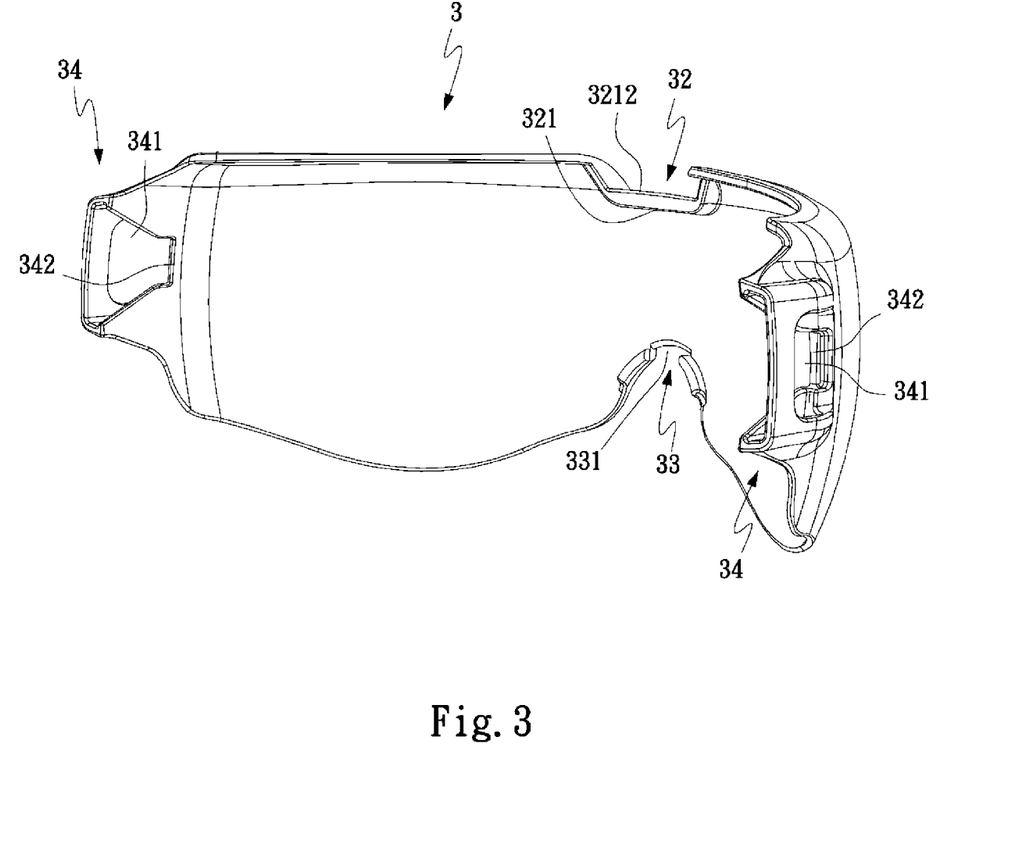
FIG. 3 is a perspective view of a lens in accordance with a preferred embodiment of the invention from another viewing angle.

With reference to FIGS. 1 and 3, FIG. 3 shows a perspective view of a lens in accordance with a preferred embodiment of the invention from another viewing angle, the lens 3 comprises a lens connecting portion 32, a lens latch portion 33 and two lens snap-in portions 34. The lens connecting portion 32 is disposed at the top of the lens 3, and the lens latch portion 33 is disposed at the bottom of the lens 3, and the two lens snap-in portions 34 are disposed on both lateral sides of the lens 3, and each lens snap-in portion 34 includes a snap-in hole 341 and an embedding edge 342.

In this preferred embodiment, the lens connecting portion 32 is a notch 321 having an internal notch rim 3211 and a flange 3212 disposed at the bottom of the notch 321, and the lens latch portion 33 includes a latch groove 331, and the latch protrusion 231 and the latch groove 331 are in a backwardly tapered shape.

Figure 5:
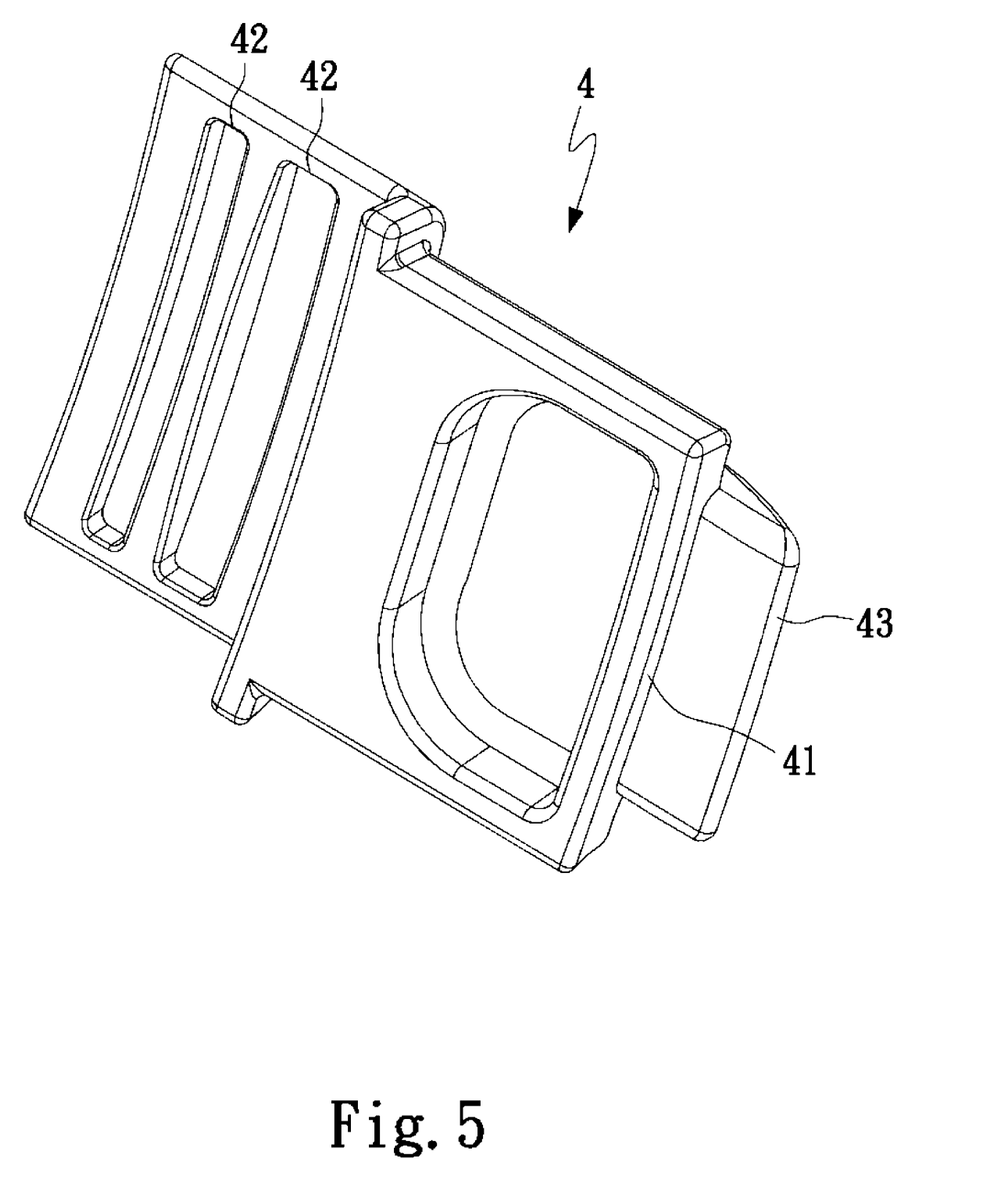
FIG. 5 is a perspective view of an elastic buckle in accordance with a preferred embodiment of the present invention from another viewing angle.

With reference to FIGS. 4 and 5, FIG. 4 shows a perspective view of an elastic buckle in accordance with a preferred embodiment of the present invention and FIG. 5 shows a perspective view of an elastic buckle in accordance with a preferred embodiment of the present invention from another viewing angle. Each of the two elastic buckles 4 has a top pressing edge 41, at least one connecting hole 42, a wedge-shaped connector 43 and at least one wedge-shaped protrusion 44, and the wedge-shaped connector 43 can be elastically rotated along with the elastic buckle 4.

Figure 6:
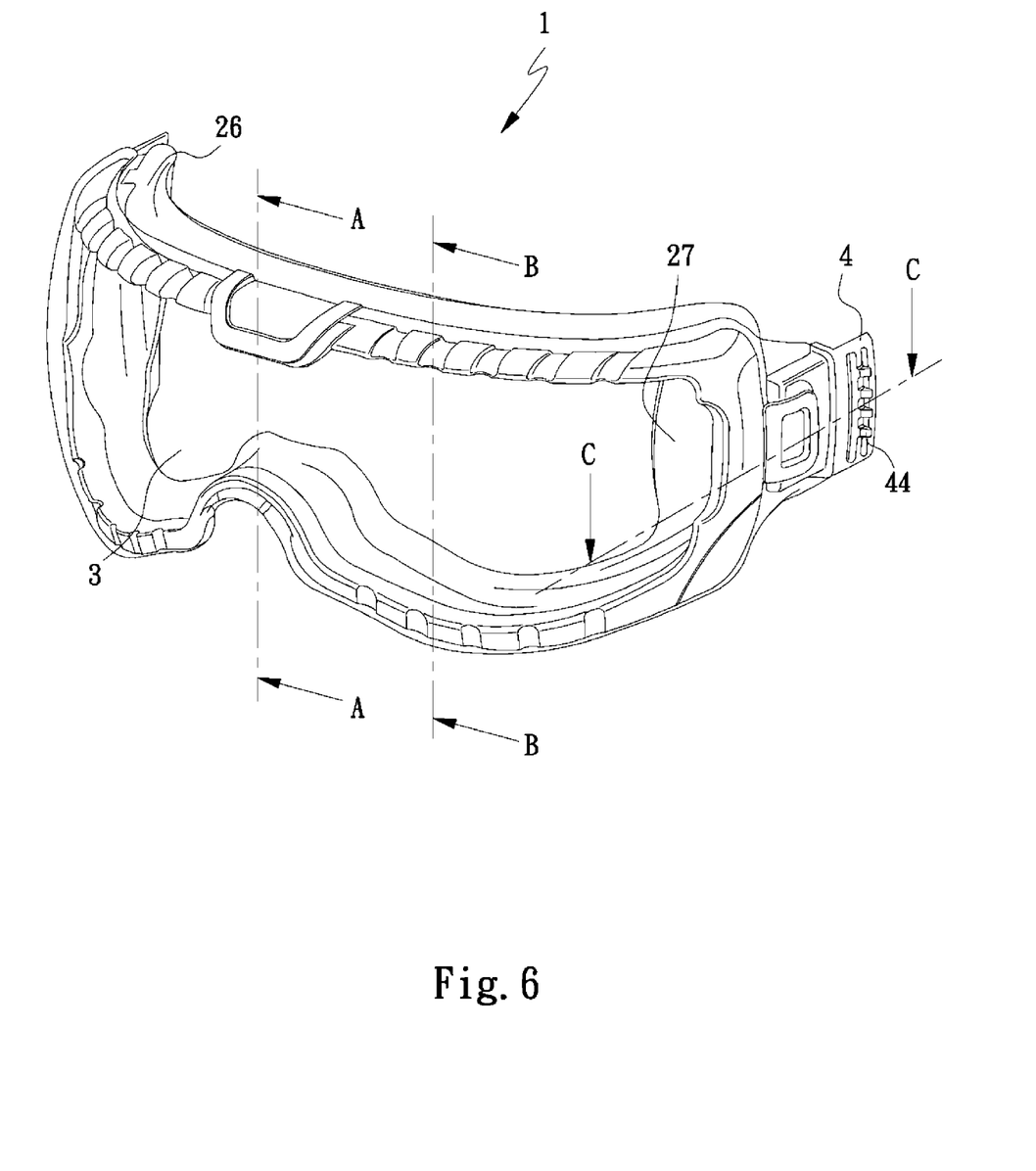
FIG. 6 is a perspective view of a preferred embodiment of the invention.
Figure 7:
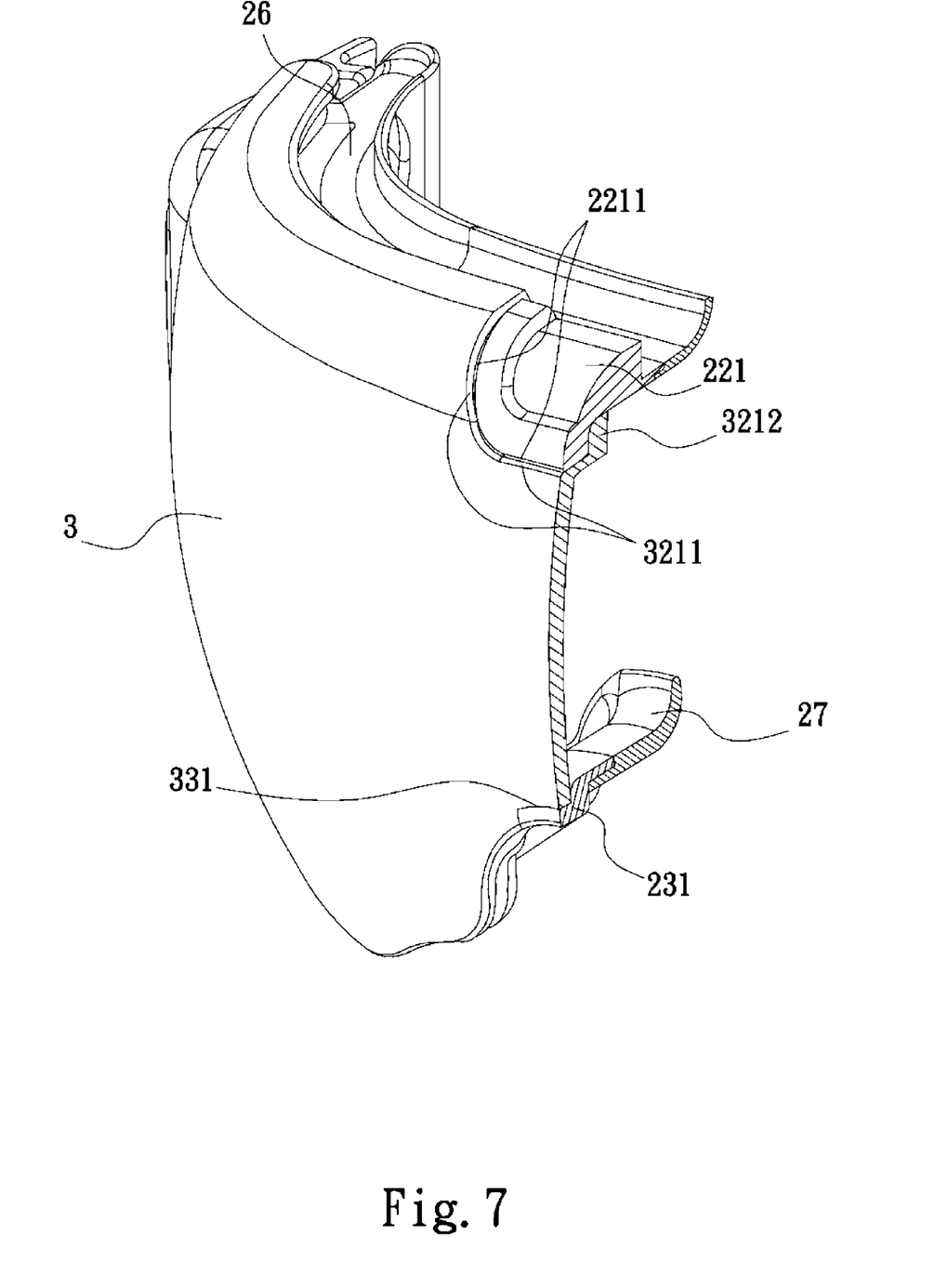
FIG. 7 is a cross-sectional view of Section A-A of FIG. 6.
Figure 8:
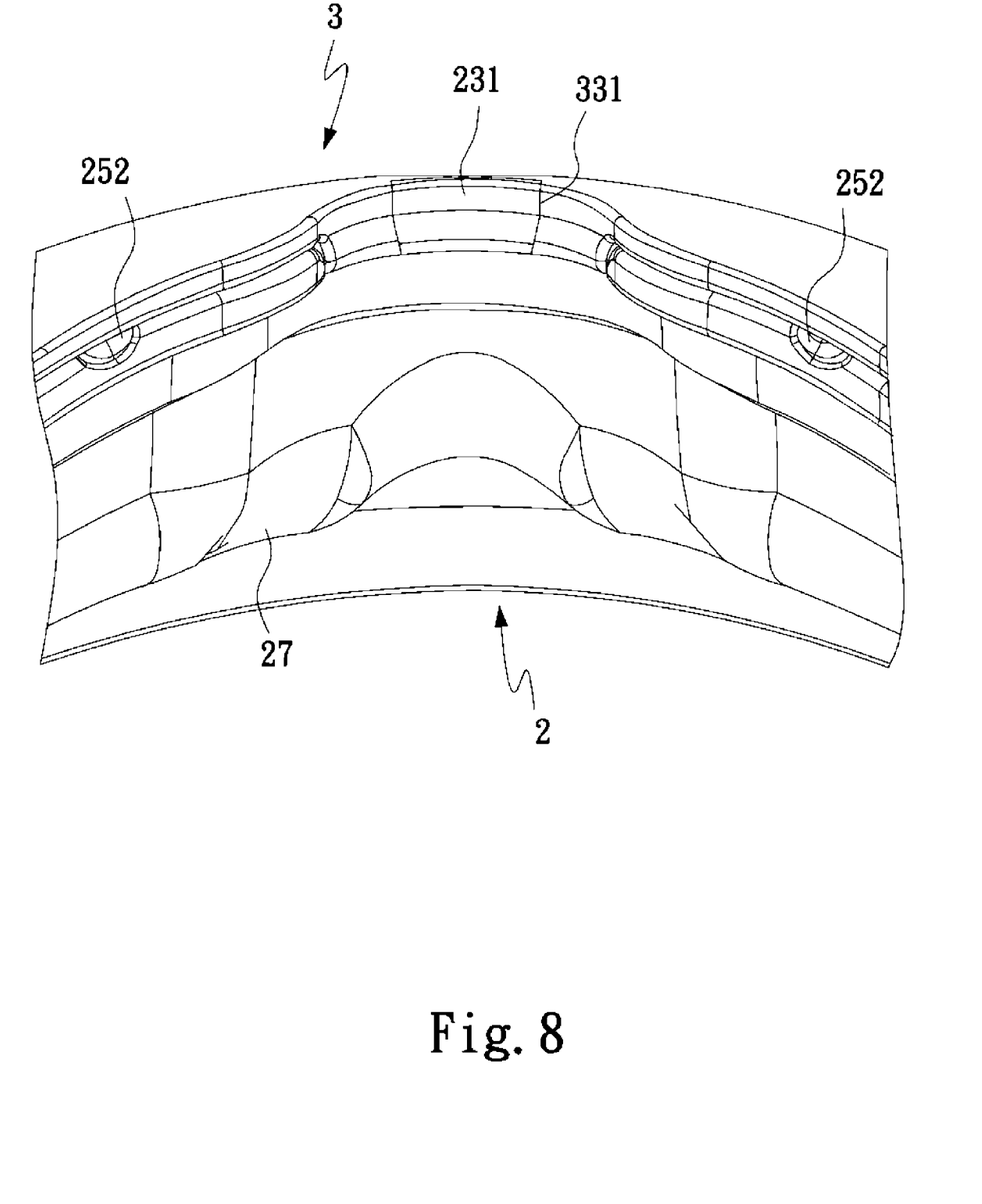
FIG. 8 is a bottom view of a portion of FIG. 6.
Figure 9:
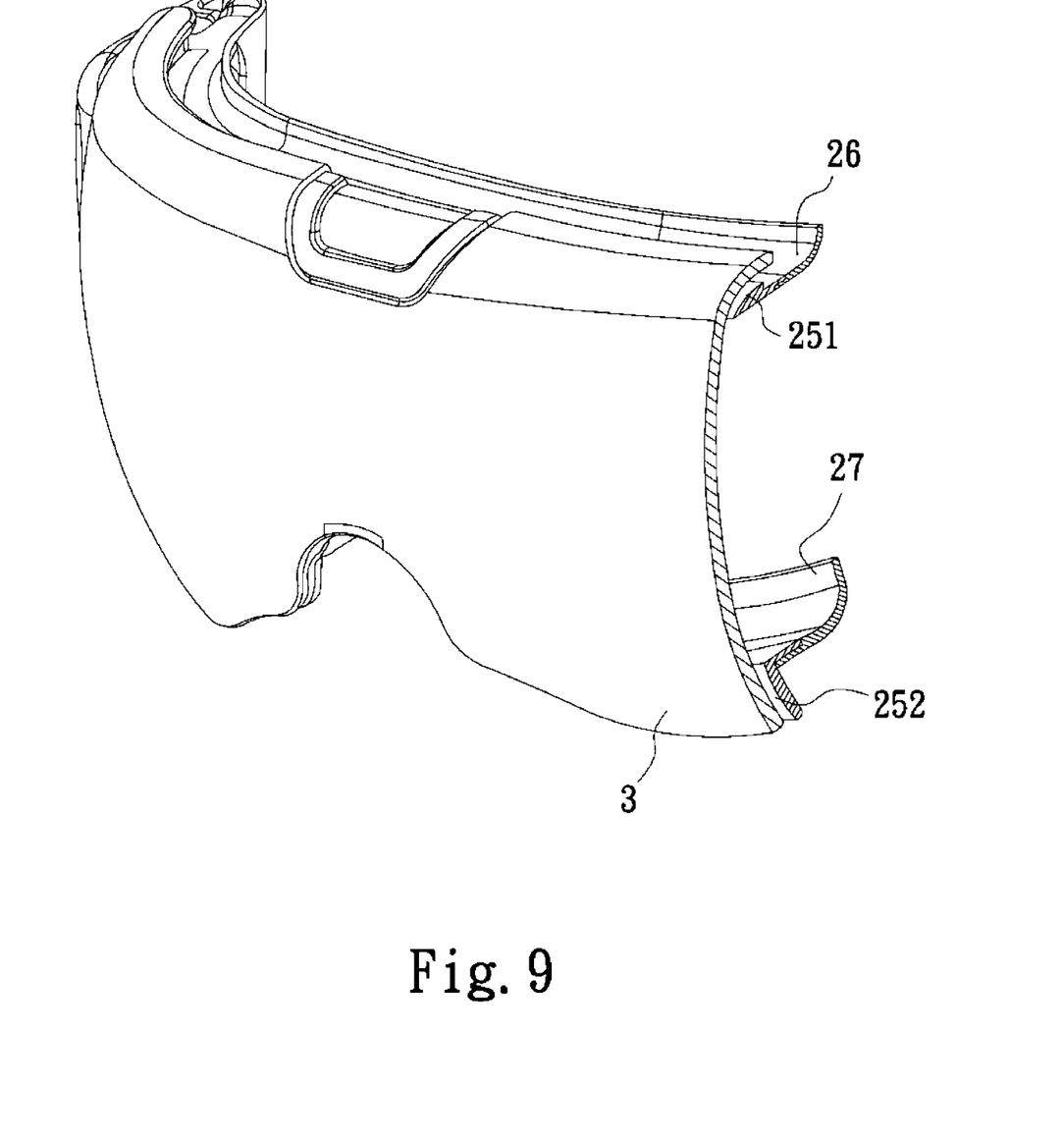
FIG. 9 is a cross-sectional view of Section B-B of FIG. 6.
Figure 10:
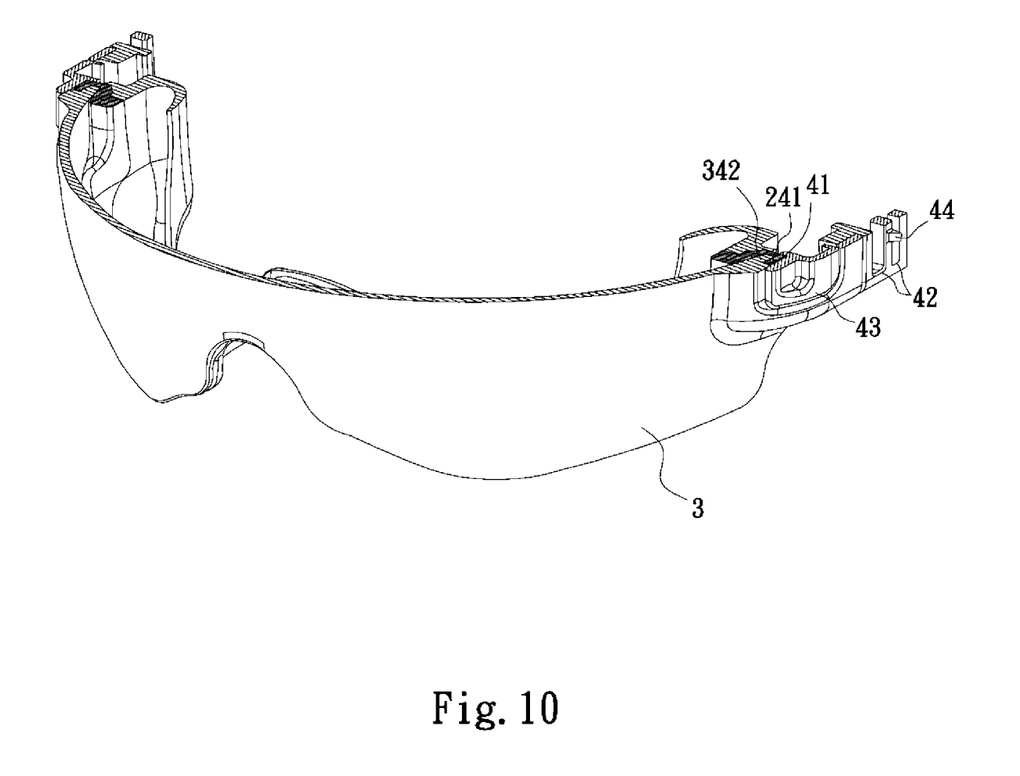
FIG. 10 is a cross-sectional view of Section C-C of FIG. 6.

With reference to FIGS. 1 to 5 as well as FIGS. 6 to 10, FIG. 6 shows a perspective view of a preferred embodiment of the present invention, and FIG. 7 shows a cross-sectional view of Section A-A of FIG. 6, and FIG. 8 shows a bottom view of a portion of FIG. 6, and FIG. 9 shows a cross-sectional view of Section B-B of FIG. 6, and FIG. 10 shows a cross-sectional view of Section C-C of FIG. 6.

When the lens 3 and the frame 2 are assembled, the lens 3 is covered onto the opening 21 and the periphery of the lens 3 is covered onto the upper guide channel 251 and the lower guide channel 252, and the lens connecting portion 32 of the lens 3 is latched to the frame connecting portion 22 of the frame 2, and the lens latch portion 33 of the lens 3 is latched to the frame latch portion 23 of the frame 2, and the two lens snap-in portions 34 of the lens 3 are snapped into the two frame snap-in portions 24 of the frame 2. In other words, the baffle 221 of the frame connecting portion 22 is latched into the notch 321 of the lens connecting portion 32, such that the external baffle rim 2211 is attached onto the internal notch rim 3211, and the baffle 221 stops the flange 3212, and the latch groove 331 of the lens latch portion 33 is latched with the latch protrusion 231 of the frame latch portion 23, and the two L-shaped embedding hooks of the frame 2 are embedded with the two embedding edges 342 of the lens 3 respectively.

When the lens 3 and the frame 2 are assembled, the lens 3 is tilted slightly such that the baffle 221 of the frame connecting portion 22 is latched to the notch 321 of the lens connecting portion 32, such that the external baffle rim 2211 is attached with the internal notch rim 3211, and the baffle 221 stops the flange 3212. If it is necessary to move the lens 3 forward, the forward movement of the lens 3 will be limited, since the baffle 221 stops the flange 3212. If it is necessary to move the lens 3 backward or downward, the backward and downward movements of the lens 3 will be limited, since the lens 3 is covered onto the periphery of the frame 2. If it is necessary to move the lens 3 to the left or the right, the external baffle rim 2211 will limit the left and right movements of the internal notch rim 3211, since the baffle 221 is latched with the notch 321. Therefore, the left and right movements of the lens 3 are limited. If it is necessary to move the lens 3 upward, the external baffle rim 2211 will limit the upward movement of the bottom of the notch 321, since the baffle 221 is latched with the notch 321. Therefore, the upward movement of the lens 3 will be limited. In summation, the movements of the lens 3 in six directions are all limited, and thus the lens 3 is mounted onto the frame 2. The bottom of the lens 3 is pushed gently to latch the latch groove 331 of the lens latch portion 33 with the latch protrusion 231 of the frame latch portion 23 of the frame 2. Since the latch protrusion 231 and the latch groove 331 come with a backwardly tapered design (as shown in FIG. 8), the forward movement of the bottom of the lens 3 is limited, therefore the lens 3 can be mounted onto the frame 2.

After the lens 3 is mounted onto the frame 2, each elastic buckle 4 is inserted and snapped into each snap-in hole 341 of the lens 3, and each top pressing edge 41 abuts each stop portion 241 of the frame 2, and the rear edge of each wedge-shaped connector 43 abuts the rear edge of each snap-in hole 341. In the foregoing process, the wedge-shaped connector 43 of the elastic buckle 4 is elastic, such that when the wedge-shaped connector 43 of the elastic buckle 4 is inserted into the snap-in hole 341, the wedge-shaped connector 43 can be turned elastically and slightly first and then inserted into the snap-in hole 341. After the wedge-shaped connector 43 is inserted into the snap-in hole 341, the elastic wedge-shaped connector 43 resumes its original position to latch the snap-in hole 341. Further, the rear edge of the wedge-shaped connector 43 of the elastic buckle 4 abuts the rear edge of the snap-in hole 341 of the lens 3, and the top pressing edge 41 of the elastic buckle 4 abuts the stop portion 241 of the frame 2, such that the lens 3 can be securely mounted onto the frame 2 by the foregoing connecting and latching methods.

Figure 11:
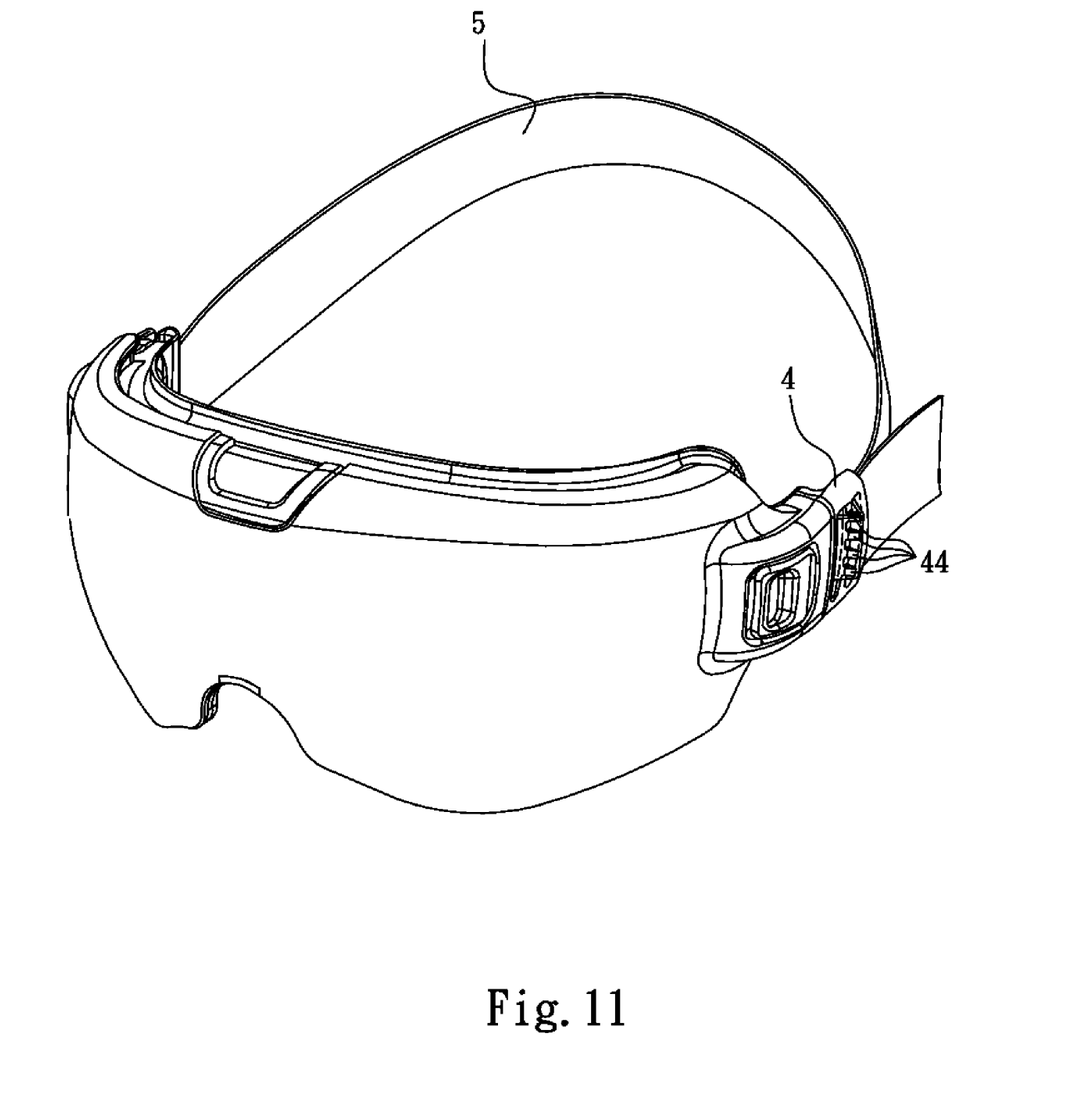
FIG. 11 is a schematic view of an application mode in accordance with a preferred embodiment of the invention.

With reference to FIGS. 1 to 10 as well as FIG. 11, FIG. 11 shows a schematic view of an application mode of a safety goggles structure in accordance with a preferred embodiment of the invention, the safety goggles structure 1, the frame 2 further comprises a circular flexible edge 27 disposed around the rear side of the frame 2, and the two elastic buckles 4 have two connecting holes 42 for separately connecting to both ends of a headband 5. When the safety goggles structure is used, the headband 5 is provided for a user's head (not shown in the figure) to wear the safety goggles. With the circular flexible edge 27, the frame 2 is in contact with a worker's head tightly and comfortably. In addition, the two elastic buckles 4 have at least one wedge-shaped protrusion 44 separately for stopping the headband 5 from sliding. In FIG. 11, the wedge-shaped protrusions 44 are disposed on the external side of the elastic buckle 4. Of course, the wedge-shaped protrusions 44 can be designed to be disposed on the internal side of the elastic buckle 4 as well.

In summation, the design of various latching structures in accordance with the present invention provides a secured connection of the frame 2 and the lens 3 of the safety goggles structure 1, such that the frame 2 or the lens 3 will not separate from each other when a user wears or removes a goggle, or removes the elastic buckle 4 for cleaning or maintenance, so that the frame 2 or the lens 3 will not be damaged by falling down onto the ground.

With the upwardly tapered upper guide channel 251 slantingly and concavely disposed at the top of the front side of the frame 2 and the upwardly tapered lower guide channel 252 disposed at the bottom of the front side of the frame 2, air enters from the bottom and discharges from the top to achieve the purpose of circulating air when a user wears the safety goggles structure 1. In other words, the lens 3 will not produce fogs. With the foregoing slanting design, foreign substances such as dusts, pebbles and liquid splashes will not enter into the safety goggles or damage the eyes of a worker. In addition, the upper guide channel 251 and the lower guide channel 252 come with an upwardly tapered design. Based on the conservation of mass, when air flows from a large cross-sectional area to a small cross-sectional area, the speed of airflow becomes larger, such that a jet flow is formed when the air enters into the lens 3 first and then discharges from the lens 3, so as to improve the anti-fog efficiency in the lens 3 as well as the heat dissipating efficiency in the lens 3.

With the upwardly tapered design of the upper guide channel 251 and the design of the upper gutter 26, liquid splashed onto the safety goggles will not enter into the safety goggles easily, since the upwardly tapered upper guide channel 251 provides a small outlet for discharging the airflow. The liquid splashes will flow down along both lateral sides of the upper gutter 26 without causing the issue of accumulating liquid. If liquid overflows from the upper guide channel 251 into the safety goggles, the liquid will flow down along the slanting and concaved upper guide channel 251 and the internal surface of the lens 3 to the lower guide channel 252 vertically up-and-down and concavely disposed at the bottom so as to effectively avoid liquid from contacting a wearer's eyes.

In summation of the description above, the present invention improves the connecting stability and prevents fogs, liquid accumulations and leaks by an improved structural design, and complies with the patent application requirements, and thus is duly filed for patent application.

While the invention has been described by means of specific embodiments, numerous modifications and variations could be made thereto by those skilled in the art without departing from the scope and spirit of the invention set forth in the claims.

What is claimed is:

1. A safety goggles structure, comprising:
a frame, being in a ring-shape, and having an opening disposed around the frame, a frame connecting portion, a frame latch portion, two frame snap-in portions, at least one upper guide channel, at least one lower guide channel and an upper gutter, and the frame connecting portion being disposed on the top of the frame, and the frame latch portion being disposed at the bottom of the frame, and the two frame snap-in portions being disposed on both lateral sides of the frame respectively, and the upper guide channel being slantingly and concavely disposed at the top of the front side of the frame and interconnected to the opening and the exterior of the frame, and the lower guide channel being vertically up-and-down and concavely disposed at the bottom of the front side of the frame and interconnected to the opening and the exterior of the frame, and the upper gutter being concavely disposed on an upper side of the frame, and the two frame snap-in portions having a stop portion separately;
a lens, covered onto the opening, and having a periphery covered onto the upper guide channel and the lower guide channel, and including a lens connecting portion, a lens latch portion and two lens snap-in portions, and the lens connecting portion being disposed at the top of the lens and latched with the frame connecting portion, and the lens latch portion being disposed at the bottom of the lens and latched with the frame latch portion, and the two lens snap-in portions being disposed on both lateral sides of the lens and snapped into the two frame snap-in portions respectively, and the two lens snap-in portions having a snap-in hole separately; and
two elastic buckles, each having a top pressing edge, and the two elastic buckles being inserted and snapped into the two snap-in holes respectively, and the two top pressing edges abutting the two stop portions respectively.

2. The safety goggles structure of claim 1, wherein the upper guide channel is upwardly tapered, and the lower guide channel is upwardly tapered.

3. The safety goggles structure of claim 1, wherein the lens connecting portion is a notch having an internal notch rim and a flange disposed at the bottom of the notch, and the frame connecting portion is a baffle having an internal baffle rim, and the baffle is latched to the notch, and the external baffle rim is attached with the internal notch rim, and the baffle stops the flange.

4. The safety goggles structure of claim 1, wherein the frame latch portion includes a latch protrusion, and the lens latch portion includes a latch groove, and the latch protrusion and the latch groove are in a backwardly tapered shape.

5. The safety goggles structure of claim 1, wherein the two stop portions are L-shaped embedding hooks, and the two lens snap-in portions further include embedding edges for embedding the two L-shaped embedding hooks respectively.

6. The safety goggles structure of claim 1, wherein the frame further includes a circular flexible edge disposed around the rear side of the frame.

7. The safety goggles structure of claim 1, wherein the two elastic buckles further comprise at least one connecting hole.

8. The safety goggles structure of claim 7, further comprising a headband, and the connecting holes are disposed on both ends of the headband respectively.

9. The safety goggles structure of claim 8, wherein the two elastic buckles further comprise at least one wedge-shaped protrusion for stopping the headband.

10. The safety goggles structure of claim 1, wherein the two elastic buckles further include an elastic rotating wedge-shaped connector disposed at the two snap-in holes respectively.

11. The safety goggles structure of claim 1, wherein the front portion of the frame is made of a hard material and the rear portion of the frame is made of a soft material.

* * * * *